United States Patent
Hansen et al.

(10) Patent No.: US 9,592,397 B2
(45) Date of Patent: Mar. 14, 2017

(54) THERMAL MANAGEMENT FOR IMPLANTABLE WIRELESS POWER TRANSFER SYSTEMS

(71) Applicant: Thoratec Corporation, Pleasanton, CA (US)

(72) Inventors: John Freddy Hansen, Pleasanton, CA (US); Joseph C. Stark, III, San Leandro, CA (US)

(73) Assignee: Thoratec Corporation, St. Paul, MN (US)

( * ) Notice: Subject to any disclaimer, the term of this patent is extended or adjusted under 35 U.S.C. 154(b) by 0 days.

(21) Appl. No.: 13/953,547

(22) Filed: Jul. 29, 2013

(65) Prior Publication Data

US 2014/0031606 A1    Jan. 30, 2014

Related U.S. Application Data

(60) Provisional application No. 61/676,626, filed on Jul. 27, 2012, provisional application No. 61/790,556, filed on Mar. 15, 2013.

(51) Int. Cl.
*A61M 1/12*    (2006.01)
*A61N 1/375*   (2006.01)
(Continued)

(52) U.S. Cl.
CPC ............. *A61N 1/375* (2013.01); *A61M 1/12* (2013.01); *A61M 1/127* (2013.01);
(Continued)

(58) Field of Classification Search
CPC .... A61N 1/375; A61N 1/3754; A61N 1/3756; A61N 1/3986; A61N 1/3758;
(Continued)

(56) References Cited

U.S. PATENT DOCUMENTS 4,041,955 A * 8/1977 Kelly et al. ............. 607/36
4,352,960 A   10/1982 Dormer et al.
(Continued)

FOREIGN PATENT DOCUMENTS

DE   202012000166 U1   6/2013
DE   102012201073 A1   7/2013
(Continued)

OTHER PUBLICATIONS

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.
(Continued)

*Primary Examiner* — Edward Moran
*Assistant Examiner* — Pamela M Bays
(74) *Attorney, Agent, or Firm* — Armstrong Teasdale LLP (57) ABSTRACT

Thermal management solutions for wireless power transfer systems are provided, which may include any number of features. In one embodiment, an implantable wireless power receiver includes at least one thermal layer disposed on an interior surface of the receiver configured to conduct heat from a central portion of the receiver towards edges of the receiver. The thermal layer can comprise, for example, a copper layer or a ceramic layer embedded in an acrylic polymer matrix. In some embodiments, a plurality of thermal channels can be formed within the receiver to transport heat from central regions of the receiver towards edges of the receiver via free convection. In yet another embodiment, a fluid pipe can be connected to the receiver and be configured to carry heat from the receiver to a location remote from the receiver. Methods of use are also provided.

33 Claims, 7 Drawing Sheets

(51) Int. Cl.
*H05K 7/20* (2006.01)
*A61N 1/39* (2006.01)

(52) U.S. Cl.
CPC .......... *H05K 7/2039* (2013.01); *A61N 1/3758* (2013.01); *A61N 1/3968* (2013.01); *H05K 7/20409* (2013.01)

(58) Field of Classification Search
CPC ...... A61N 1/3787; H05K 7/20; H05K 7/2039; H05K 7/20409; H05K 7/20436; A61M 1/12; A61M 1/127; H01L 23/36
USPC .............................................. 607/16, 36, 63
See application file for complete search history.

(56) References Cited

U.S. PATENT DOCUMENTS

| | | |
|---|---|---|
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 5,346,458 A | 9/1994 | Affeld |
| 5,350,413 A | 9/1994 | Miller |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1* | 11/2001 | Sato et al. ..................... 463/44 |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 5/2005 | Amundson et al. |
| 6,949,065 B2 | 9/2005 | Sporer et al. |
| 6,960,968 B2 | 11/2005 | Odendaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | LaFranchise et al. |
| 7,565,187 B1 | 7/2009 | Dynok et al. |
| 7,571,007 B2 | 8/2009 | Erickson et al. |
| 7,574,173 B2 | 8/2009 | Terranova et al. |
| 7,587,241 B2 | 9/2009 | Parramon et al. |
| 7,599,743 B2 | 10/2009 | Hassler et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,741,734 B2 | 6/2010 | Joannopoulos et al. |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson |
| 7,962,222 B2 | 6/2011 | He et al. |
| RE42,682 E | 9/2011 | Barreras et al. |
| 8,076,801 B2 | 12/2011 | Karalis et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbanaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Sample et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,810,071 B2 | 8/2014 | Sauerlaender et al. |
| 8,884,468 B2 | 11/2014 | Lemmens et al. |
| 8,971,958 B2 | 3/2015 | Frikart et al. |
| 9,002,468 B2 | 4/2015 | Shea et al. |
| 9,106,083 B2 | 8/2015 | Partovi |
| 9,192,704 B2 | 11/2015 | Yomtov et al. |
| 2002/0038138 A1 | 3/2002 | Zarinetchi et al. |
| 2002/0087204 A1 | 7/2002 | Kung et al. |
| 2002/0093456 A1 | 7/2002 | Sawamura et al. |
| 2003/0171792 A1 | 9/2003 | Zarinetchi et al. |
| 2004/0138725 A1 | 7/2004 | Forsell |
| 2004/0256146 A1 | 12/2004 | Fricks |
| 2005/0006083 A1* | 1/2005 | Chen et al. ................... 165/185 |
| 2005/0288743 A1 | 12/2005 | Ahn et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |

(56) References Cited

U.S. PATENT DOCUMENTS

| | | |
|---|---|---|
| 2008/0027293 A1 | 1/2008 | Vodermayer et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0256708 A1 | 10/2010 | Thornton et al. |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | DiGiore et al. |
| 2011/0025132 A1 | 2/2011 | Sato |
| 2011/0043050 A1 | 2/2011 | Yabe et al. |
| 2011/0046699 A1 | 2/2011 | Mazanec |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1* | 12/2011 | Wells et al. ............. 607/89 |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0127253 A1 | 5/2013 | Stark et al. |
| 2013/0159956 A1 | 6/2013 | Verghese et al. |
| 2013/0190551 A1 | 7/2013 | Callaway et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2016/0218432 A1 | 7/2016 | Pope et al. |
| 2016/0250484 A1 | 9/2016 | Nguyen et al. |
| 2016/0254703 A1 | 9/2016 | Hansen |
| 2016/0254704 A1 | 9/2016 | Hansen et al. |

FOREIGN PATENT DOCUMENTS

| | | |
|---|---|---|
| EP | 1513241 A1 | 3/2005 |
| JP | H03109063 A | 5/1991 |
| JP | 11-506646 | 6/1999 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120007296 | 1/2012 |
| KR | 1020120077448 | 7/2012 |
| WO | 0001442 A2 | 1/2000 |
| WO | WO00/74747 A1 | 12/2000 |
| WO | WO01/37926 A1 | 5/2001 |
| WO | WO2005/106901 A2 | 11/2005 |
| WO | 2007053881 A1 | 5/2007 |
| WO | WO2008/066941 A2 | 6/2008 |
| WO | WO2009/018271 A1 | 2/2009 |
| WO | WO2009/021220 A1 | 2/2009 |
| WO | WO2009/023905 A1 | 2/2009 |
| WO | WO2009/042977 A1 | 4/2009 |
| WO | WO2010/030378 A1 | 3/2010 |
| WO | WO2010/089354 A2 | 8/2010 |
| WO | 2011081626 A1 | 7/2011 |
| WO | WO2011/113934 A1 | 9/2011 |
| WO | WO2012/002063 A1 | 1/2012 |
| WO | WO2012/056365 A2 | 5/2012 |
| WO | WO2012/087807 A2 | 6/2012 |
| WO | WO2012/087811 A2 | 6/2012 |
| WO | WO2012/087816 A2 | 6/2012 |
| WO | WO2012/087819 A2 | 6/2012 |
| WO | 2012099965 A2 | 7/2012 |
| WO | WO2012/141752 A2 | 10/2012 |
| WO | 2013110602 A1 | 8/2013 |
| WO | WO2013/138451 A1 | 9/2013 |
| WO | WO2014/039673 A1 | 3/2014 |

(56) References Cited

FOREIGN PATENT DOCUMENTS

OTHER PUBLICATIONS

Chargepoint, Inc.; -chargepoin+®; product brochure; 4 pgs.; © 2014; retrieved Mar. 12, 2014 from the Internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filed and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Petersen et al.; U.S. Appl. No. 14/414,708 entitled "Wireless Battery Charging," filed Jan. 14, 2015.

Petersen, E.; U.S. Appl. No. 14/414,820 entitled "Variable Capacitor for Resonant Power Transfer Systems," filed Jan. 14, 2015.

Petersen, E.; U.S. Appl. No. 14/414,823 entitled "Resonant Power Transfer System and Method of Estimating System State," filed Jan. 14, 2015.

Hansen, J.; U.S. Appl. No. 14/414,832 entitled "Resonant Power Transfer Systems With Protective Algorithm," filed Jan. 14, 2015.

Petersen et al.; U.S. Appl. No. 14/414,840 entitled "Computer Modeling for Resonant Power Transfer Systems," filed Jan. 14, 2015.

Hansen, J.; U.S. Appl. No. 14/414,842 entitled "Resonant Power Transmission Coils and Systems," filed Jan. 14, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al., "The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

Notification of Transmittal of the International Search Report and the Written Opinion of the International Searching Authority for PCT Application No. PCT/US2015/051474, mailed Dec. 30, 2015.

* cited by examiner

$$k \approx \frac{A_2}{A_1}$$

Fig. 3A

$$k \approx \frac{A_2}{A_1} \cos\theta$$

THERMAL MANAGEMENT FOR IMPLANTABLE WIRELESS POWER TRANSFER SYSTEMS

CROSS-REFERENCE TO RELATED APPLICATIONS

This application claims the benefit of U.S. Provisional Patent Application No. 61/676,626, filed Jul. 27, 2012, titled "Thermal Management for Implantable Wireless Power Transfer Systems", and U.S. Provisional Patent Application No. 61/790,556, filed Mar. 15, 2013, titled "Thermal Management for Implantable Wireless Power Transfer Systems".

INCORPORATION BY REFERENCE

All publications and patent applications mentioned in this specification are herein incorporated by reference to the same extent as if each individual publication or patent application was specifically and individually indicated to be incorporated by reference.

FIELD

The field relates generally to resonant wireless power transfer systems, and more specifically to implantable resonant wireless power transfer systems.

BACKGROUND

Transferring power from an external device to an implanted device wirelessly with a Transcutaneous Energy Transfer (TET) system via, e.g., an oscillating magnetic field, generates heat, which can cause a temperature rise in the device itself and/or in any surrounding material.

Furthermore, an implanted device may require local electrical energy storage and processing when external power is interrupted or not available. This electrical energy processing and storage, typically solid-state electronics and a battery, generate heat while operating the implant, and especially when the battery is charging or discharging. For implantable medical devices, the associated temperature rise of the implant should be kept less than 2° C. to avoid tissue damage.

Many implantable medical devices, such as implanted sensors, require very little power to operate. With such low power levels (on the order of milliwatts), temperature rise within the implant is not a concern as the temperature rise easily remains below the 2° C. threshold. With higher power devices (e.g., on the order of watts and up to 15 W or more), temperature rise is a larger concern.

Electrical devices that are powered wirelessly and require more power are typically not implanted in human patients. For example, cell phones and laptops can heat up much more than 2° C. when being charged, but these temperatures are considered acceptable since they are not implantable devices.

SUMMARY OF THE DISCLOSURE

A power receiver of a wireless power transfer system is provided, comprising an implantable housing, a receiver coil supported by the implantable housing, electronics disposed within the implantable housing and coupled to the receiver coil, the electronics configured to control wireless power transfer from an external power transmitter to the receiver coil, and at least one thermal layer disposed on an interior surface of the implantable housing, the at least one thermal layer configured to conduct heat from a central portion of the implantable housing towards edges of the implantable housing.

In some embodiments, the at least one thermal layer comprises at least one copper layer. In another embodiment, the at least one thermal layer comprises a pair of thermal layers disposed on opposing internal sides of the implantable housing.

In one embodiment, the at least one thermal layer comprises a thickness of less than 0.5 mm copper. In another embodiment, the at least one thermal layer comprises a thickness of less than 1 mm aluminum.

In some embodiments, a central portion of the at least one thermal layer comprises a silicon rubber material. In another embodiment, the at least one thermal layer comprises a copper layer having a central portion comprising a silicon rubber material.

In some embodiments, the at least one thermal layer comprises a ceramic layer embedded in an acrylic polymer matrix.

In another embodiment, the at least one thermal layer has a thickness of less than 0.5 mm.

A power receiver of a wireless power transfer system is also provided, comprising an implantable housing, a receiver coil supported by the implantable housing, at least one power converter disposed within the implantable housing and coupled to the receiver coil, a plurality of electronics disposed within the implantable housing and coupled to the receiver coil and the power converter, the electronics configured to control wireless power transfer from an external power transmitter to the at least one power converter, and a plurality of thermal channels formed by an arrangement of the at least one power converter and the plurality of electronics in the implantable housing, the plurality of thermal channels configured to allow a thermal medium to transport heat from central regions of the implantable housing towards edges of the implantable housing via free convection.

In some embodiments, the thermal channels are arranged vertically with respect to gravity within the implantable housing.

In another embodiment, the power receiver comprises at least one control surface disposed in the implantable housing to further define the plurality of thermal channels.

In some embodiments, the thermal medium comprises a fluid. In other embodiments, the thermal medium comprises a gas.

A power receiver of a wireless power transfer system is provided, comprising a housing, a receiver coil supported by the housing, a plurality of electronics disposed within the housing and coupled to the receiver coil, the electronics configured to control wireless power transfer from an external power transmitter to the receiver coil, a thermal medium disposed in the housing, the thermal medium having a boiling point at a temperature greater than 38° C. but less than 45° C., and a fluid pipe coupled to an interior of the housing, the fluid pipe configured to carry a vapor generated by the thermal medium to a location remote from the housing when the thermal medium surpasses its boiling point in response to heat generated in the housing.

In some embodiments, the location remote from the housing is an implantable medical device coupled to the fluid pipe.

In one embodiment, the medical device comprises a blood pump.

In some embodiments, heat from the vapor is rejected into a blood stream of a patient.

In one embodiment, the vapor is allowed to condense at the location remote from the housing to form droplets which can be pulled back towards the power receiver to absorb heat.

In another embodiment, the fluid pipe comprises a flexible tube.

A method of reducing heat transferred to tissue by an implanted wireless power receiver is provided, comprising the steps of implanting a wireless power receiver in a patient, receiving wireless power with the wireless power receiver, and conducting heat from a central portion of the wireless power receiver towards edges of the wireless power receiver with at least one thermal layer disposed on an interior surface of the wireless power receiver.

In some embodiments, the at least one thermal layer comprises at least one copper layer.

In another embodiment, the at least one thermal layer comprises a pair of thermal layers disposed on opposing internal sides of the implantable housing.

In some embodiments, the at least one thermal layer comprises a thickness of less than 0.5 mm copper. In one embodiment, the at least one thermal layer comprises a thickness of less than 1 mm aluminum. In another embodiment, a central portion of the at least one thermal layer comprises a silicon rubber material. In another embodiment, the at least one thermal layer comprises a copper layer having a central portion comprising a silicon rubber material.

A method of reducing heat transferred to tissue by an implanted wireless power receiver is provided, comprising the steps of implanting a wireless power receiver in a patient, receiving wireless power with the wireless power receiver, and conducting heat from a central portion of the wireless power receiver towards edges of the wireless power receiver with a flow of a thermal medium through a plurality of thermal channels formed by an arrangement of electronics and/or batteries in the wireless power receiver.

In one embodiment, the thermal medium transports heat through the thermal channels via free convection. In another embodiment, the thermal medium comprises a fluid or a gas.

A method of reducing heat transferred to tissue by an implanted wireless power receiver is provided, comprising the steps of implanting a wireless power receiver in a patient, receiving wireless power with the wireless power receiver; heating a thermal medium disposed in the wireless power receiver in response to the receiving wireless power step, and carrying vapor generated by heating the thermal medium to a location remote from the wireless power receiver with a fluid pipe coupled to the wireless power receiver.

In some embodiments, the location remote from the wireless power receiver comprises an implantable medical device coupled to the fluid pipe.

In another embodiment, the medical device comprises a blood pump.

In one embodiment, heat from the vapor is rejected into a blood stream of a patient.

In another embodiment, the vapor is allowed to condense at the location remote from the wireless power receiver to form droplets which can be pulled back towards the wireless power receiver to absorb heat.

In some embodiments, the fluid pipe comprises a flexible tube that is routed through the patient to the location remote from the wireless power receiver.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the invention are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816;

WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, at least 0.05, at least 0.1, or at least 0.15.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Figure 1:
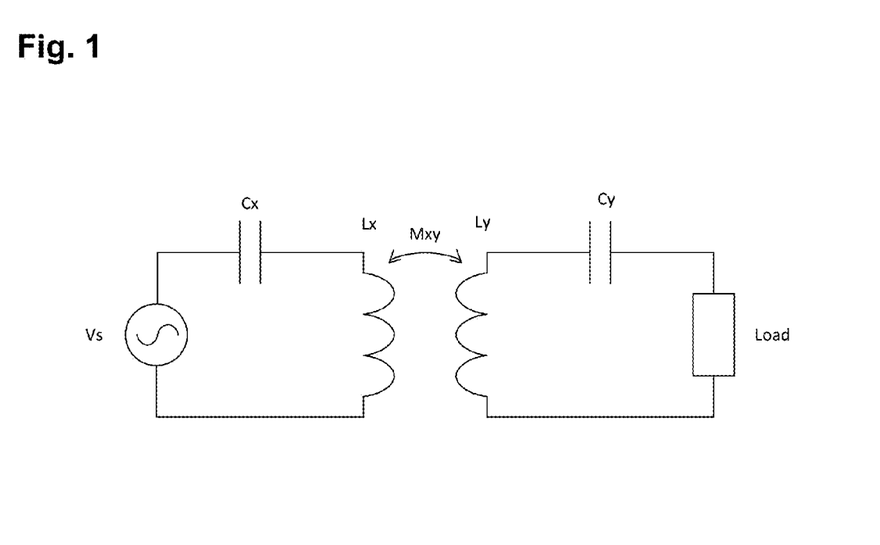
FIG. 1 illustrates a basic wireless power transfer system.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency, f, is 250 kHz. Then, for each cycle the load removes a certain amount of energy from the resonance:

$$e_L = \frac{P_L}{f} = 60 \ \mu J \ \text{Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 μJ.

The exemplary circuit was analyzed and the self inductance of the receiver coil was found to be 60 uH. From the energy and the inductance, the voltage and current in the resonator could be calculated.

$$e_y = \frac{1}{2}Li^2$$

$$i_y = \sqrt{\frac{2e_y}{L}} = 3.74A \ \text{peak}$$

$$v_y = \omega L_y i_y = 352V \ \text{peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \ \mu J}{0.05} = 8.4 \ mJ$$

For the same circuit the self inductance of the transmitter coil was 146 uH as mentioned above. This results in:

$$i_x = \sqrt{\frac{2e_x}{L}} = 10.7A \ \text{peak}$$

$$v_x = \omega L_x i_x = 2460V \ \text{peak}$$

One can appreciate from this example, the competing factors and how to balance voltage, current, and inductance to suit the circumstance and achieve the desired outcome.

Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
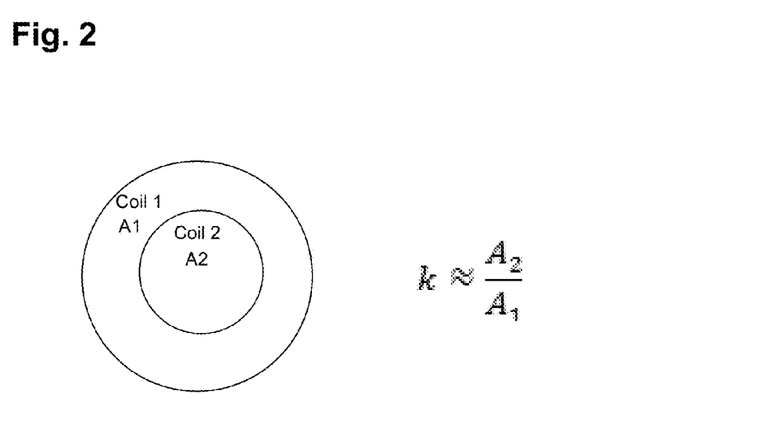
FIG. 2 illustrates the flux generated by a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
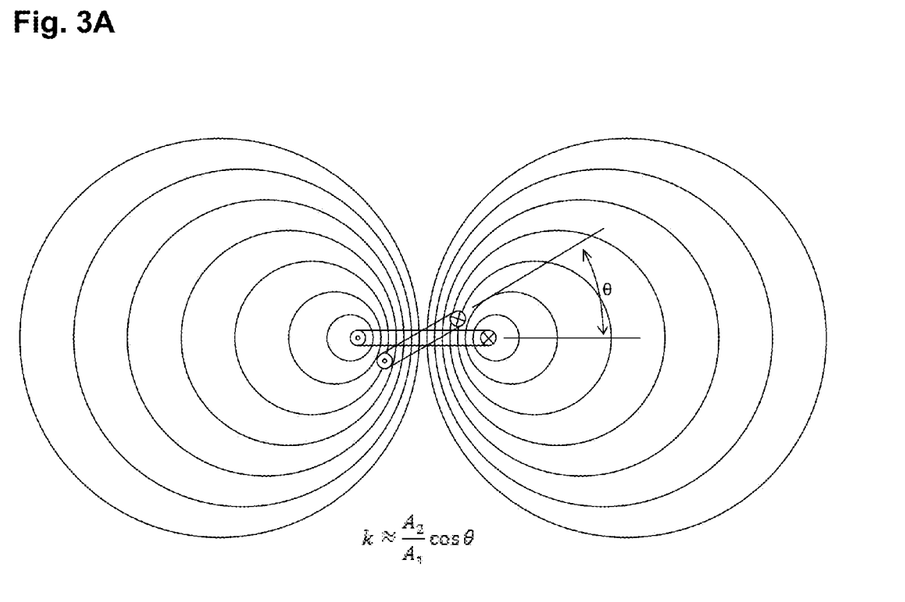
FIGS. 3A-3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta ($\theta$) is 90 degrees, the flux will not be received by the receiver and the coupling coefficient will be zero.

Figure 3B:
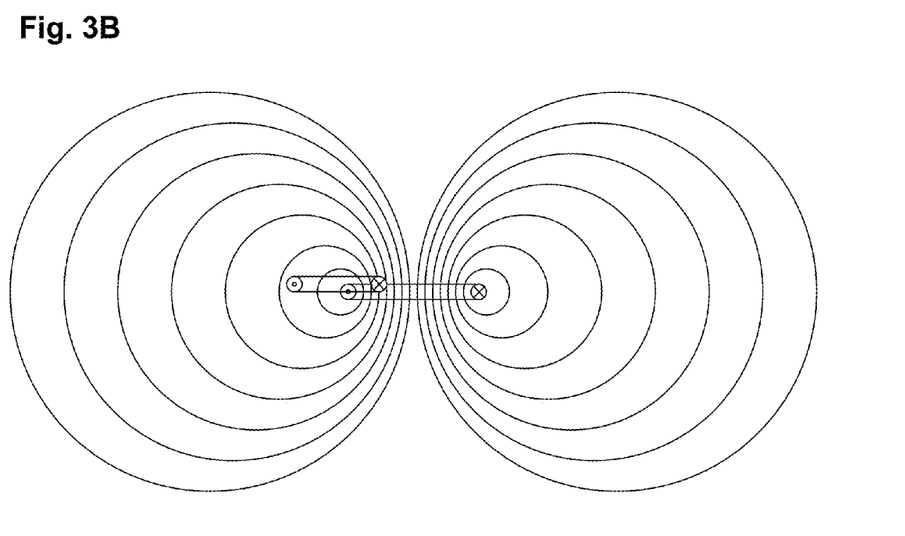

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy}=M_{yx}$$

Heat generated by implanted medical devices can cause a temperature increase in surrounding tissue. Table 1 below contains data derived from tests conducted to determine effects on different tissue types due to heat generated by implanted devices. The devices were implanted in various sites within the animal (as noted in column 2) in contact with different tissue types, and the effective thermal conductivity was calculated as shown in column 3 using an adjusted thermal conductivity that enables the inclusion of convection (in addition to conduction) when using a diffusion equation. Column 4 shows the device power setting at each site. The devices were powered for 30-60 minutes. Column 5 shows the calculated temperature rise at the hottest point at each site if the implanted device had been left powered on for many hours rather than the 30-60 minutes of each test. In some cases, the effective thermal conductivity was different on different sides of the implanted module, because the module was located between two different types of tissue. This is noted in the table where appropriate.

TABLE 1

| | Location | $k_{eff}$ [W/m · ° C.] | P [W] | $t \to \infty$: max $\Delta T$ [° C.] |
|---|---|---|---|---|
| Box A1 | R chest between skin (1.5 cm) and muscles (20 cm) | 0.66 −/+ 0.05 (skin) 0.47 −/+ 0.05 (muscle) | 5 | 8.0 +/− 0.4 |
| Box B3 | R chest between lung (20 cm) and ribs (>5 cm) | 2 −/+ 0.05 (lung) | 5 | |
| Puck A2 (D01) | R pectoral between skin (1 cm) and muscles (20 cm) | 0.25 −/+ 0.01 | 0.7 (coil) + 0.3 (caps) | 4.0 +/− 0.1 |
| Puck B1 (D03) | L posterior between muscles (2.5 cm and >6 cm) | 0.53 −/+ 0.01 | 0.7 (coil) + 0.3 (caps) | 2.9 +/− 0.1 |
| Puck B2 (D02) | L abdominal wall under rectus muscle (1.5 cm and ~20 cm) | 0.36 −/+ 0.01 | 0.7 (coil) + 0.3 (caps) | 3.0 +/− 0.1 |

Systems and methods are described herein for reducing and minimizing temperature rise in an implantable medical device resulting from wireless or Transcutaneous Energy Transfer System (TETS) power transfer. In some embodiments, thermal management within an implantable medical device is accomplished by limiting the temperature rise on the surface of the enclosure that contacts human tissue. In other embodiments, thermal management within an implantable medical device is accomplished by utilizing a thermal fluid or gas such as helium gas or transformer oil within the implant. In additional embodiments, thermal management can be accomplished using a thermal medium within the implantable medical device and a fluid pipe configured to carry vapor generated by the thermal medium away from the implant.

Figure 4A:
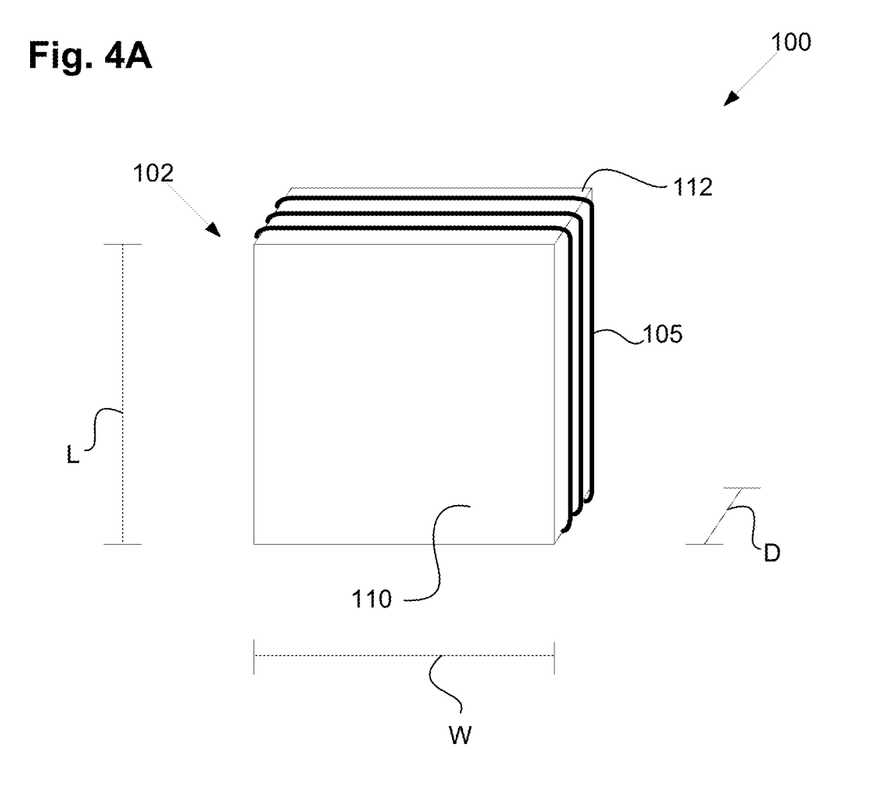
FIGS. 4A-4C illustrate various embodiments of a TETS implant having a thermal management system.

FIG. 4A is an external view of a TETS implant 100, comprising an outer housing 102. The TETS implant 100 can comprise an implantable receiver configured to receive wireless energy from a transmitter external to the patient. In some embodiments, the housing can be in the shape of a cube, with six equally shaped sides. In another embodiment, as shown in FIG. 4A, the housing 102 can comprise a cuboid shape that includes two "large" sides 110 and four "small" sides 112. Also shown in FIG. 4A is a receive coil 105 which can be configured to wirelessly receive power transmitted from an external source, such as from a transmit coil (not shown).

In some embodiments, the TETS implant can have exterior dimensions of approximately 12 cm by 10 cm by 3.5 cm, and a weight of approximately 500 g. In another embodiment, the implant can be 20 cm by 10 cm by 1.7 cm and slightly curved around the 10 cm axis, or cylindrical approximately 8 cm diameter and 1.5 cm thick. The TETS implant 100 can be a power receiver configured to communicate with a power transmitter for wireless power transmission.

Figure 4B:
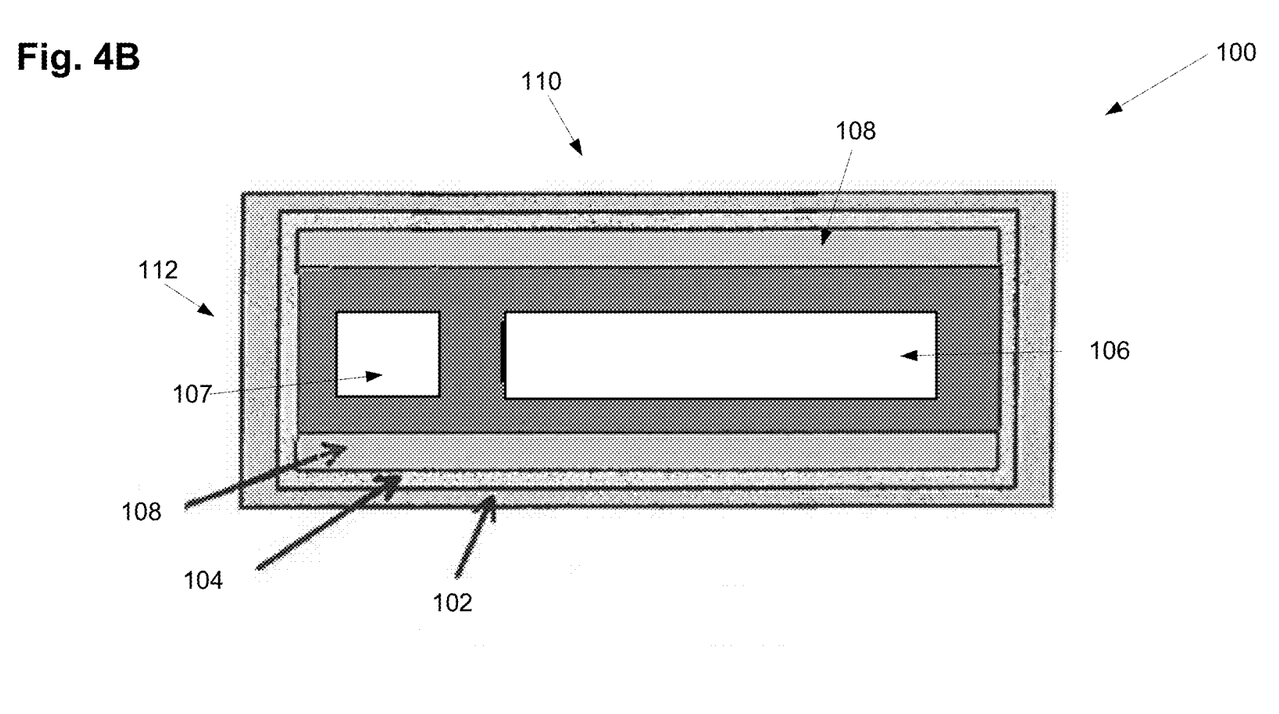

FIG. 4B is a cross-sectional view of TETS implant 100, showing the outer housing 102 and an optional inner housing 104. The inner housing 104 can be sized and shaped to conform to the inner walls of outer housing 102. As described above, the TETS implant can be configured for implantation into the human body and can include, for example, housings 102 and 104 that contains and/or supports all components needed for wireless energy transfer, such as the such as the receive coil and electronics 106 and circuitry configured to manage and control the transfer of power from the receive coil to a battery 107 in the implant. In one embodiment, the electronics can include at least one power converter disposed within the housing and coupled to the receiver coil. The electronics can be configured to control wireless power transfer from an external power transmitter to the at least one power converter and/or electronics. The TETS implant 100 can be optionally connected to other implanted medical devices within the body to provide power for those devices. In one embodiment, outer housing 102 can comprise ferrimagnetic or ferromagnetic material, such as MnZn ferrite, and inner housing 104 can comprise titanium. Receive coil 105 of FIG. 4A is not shown in FIG. 4B for ease of illustration.

Heat transfer inside the human body is dominated by conduction and convection. These processes act on temperature gradients in such a way as to round out the thermal profile, i.e., any iso-surface of constant temperature that has a high aspect ratio will, over time, become more and more spherical. Mathematically, this is particularly obvious from the diffusion equation, which states that the time derivative of the temperature is proportional to the second spatial derivative of the temperature. The diffusion equation governs heat conduction, and near the surface of an implanted device, convection can also be modeled with the diffusion equation through the use of an effective thermal conductivity tensor.

The TETS implant 100 of FIGS. 4A-4B can include a high aspect ratio between the sizes of the sides of the cuboid in order to maximize the area of the receive coil that wraps around the housing. Referring to FIG. 4A, the implant can have a relatively large length "L" and width "W" with respect to the depth "D" of the implant. Therefore, the cross-section of implant 100 can include two "large" sides 110 (with dimensions L×W) and four "small" sides 112 (with dimensions D×L or D×W). In this type of implant, heat generated inside the housing will raise the temperature the most at the center of the large sides 110.

Referring to FIG. 4B, to manage heat generated within implant 100, portions of the interior of the implant housing can be lined with at least one thermal layer 108 to dissipate heat generated by electronics 106 and battery 107. In the example shown in FIG. 4B, thermal layer 108 is disposed on the inside of housing, along the large sides 110. In the embodiment of FIG. 4B, a small gap or space is illustrated between the electronics 106 and battery 107 and the thermal layer 108. However, in other embodiments, the thermal layer 108 is positioned directly against the electronics 106 and/or battery 107.

In some embodiments, the thermal layers can comprise materials with good heat conductivity, such as copper, ceramics, silicon, rubber, silver, aluminum, beryllium, other noble metals, and even exotic materials such as diamond. However, copper is likely to be one of the most cost-effective materials with good thermal conductivity. The layer can be less than approximately 0.5 mm thick, and can comprise a flat sheet. A pair of 0.5 mm thick copper thermal layers disposed in the implant of FIG. 4B can reduce the maximum tissue temperature by approximately 1° C., for example. In one specific embodiment, the thermal layer can comprise a highly thermally conductive ceramic embedded in an acrylic polymer matrix, having an overall thickness of less than or equal to 0.25 mm and thermal conductivity of approximately 0.6 W/mK. This embodiment provides thermal conductivity, electrical isolation, and an adhesive layer for bonding internal components together By placing the thermal layers along the entire inner walls of sides 110 of the TETS implant, heat is lead from the center of the housing towards the edges of the housing. Heat release at or near the edges or corners of the housing is free to expand into a three-dimensional space, causing a lower temperature rise in the tissue of the patient than heat released near the center of the housing, where heat essentially expands one-dimensionally. It is important to note that only lining the center portion of sides 110 would not be as effective as lining the entire inner sides of the housing, since heat expansion would remain essentially one-dimensional.

In some embodiments, the electrical components within the housing can be purposefully placed away from the center of sides 110; however this may not be practical given the space constraints of the implant.

Figure 4C:
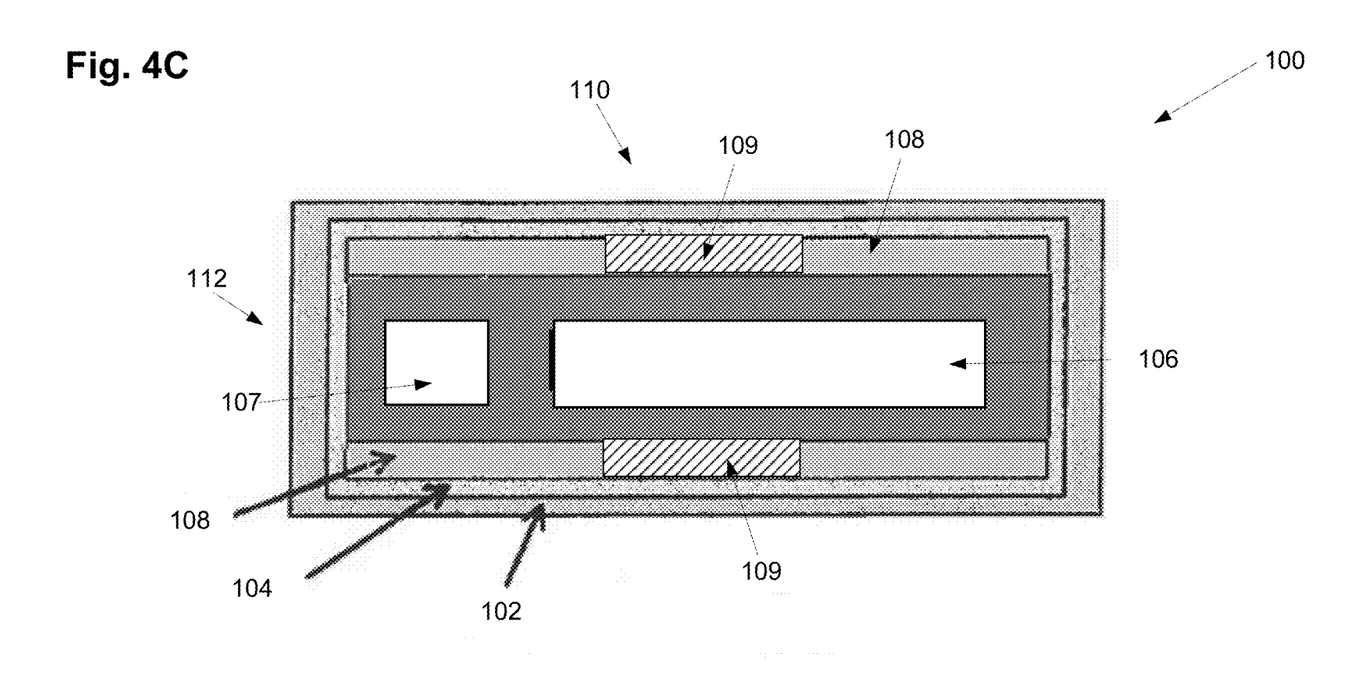

In another embodiment, shown in FIG. 4C, the thermal layer 108 can include a central portion 109 that can comprise, for example a thermal insulator such as a silicone rubber material. Utilizing a central portion 109 having a different material than thermal layer 108 can direct heat away from the center of sides 110 and towards the edges of the TETS implant. In one embodiment, central portion 109 can have a lower thermal conductivity than thermal layer 108 if it is a homogeneous material. In another embodiment, the central portion 109 can have a higher thermal conductivity in an axis connecting central portion 109 to thermal layer 108 than in an axis connecting central portion 109 to inner housing 104, which would promote heat spreading towards the edges of the housing.

Figure 5:
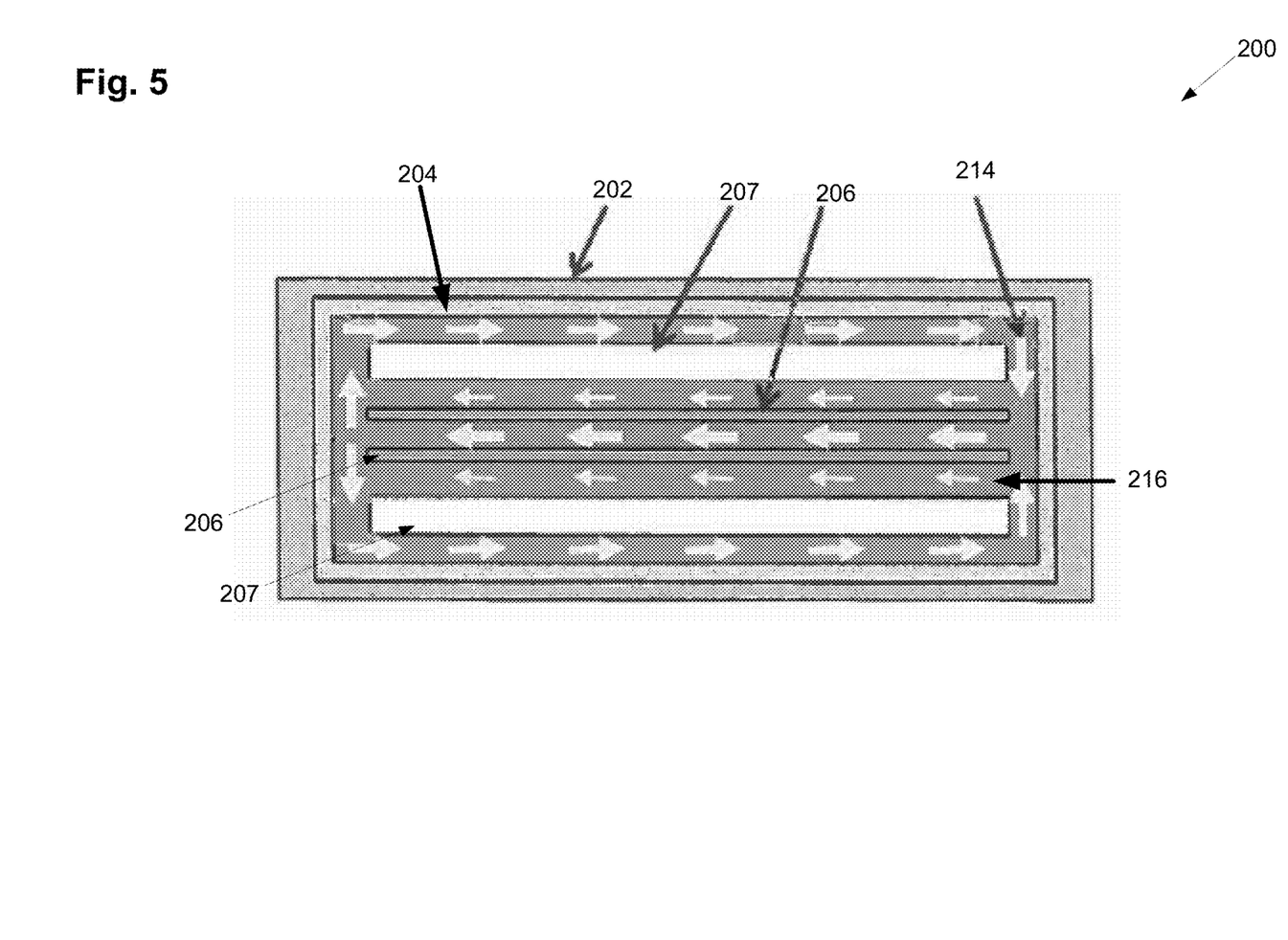
FIG. 5 illustrates another embodiment of a TETS implant having a thermal management system.

FIG. 5 illustrates another TETS implant 200 that utilizes another structure and technique for thermal management. Implant 200 can include housings 202 and 204, similar to housings 102 and 104 described above in FIGS. 4A-4B. Electronics 206 including battery 207 can be disposed within the housings of implant 200. Electronics 206 can be similar to the electronics described above and can include at least one power converter. In the embodiment shown in FIG. 5, electronics 206 and battery 207 can be arranged within the housing as shown to form a plurality of thermal channels 216 between the individual battery and electronics components. In FIG. 5, the channels 216 are formed by two separate electronics 206 and batteries 207, however it should be understood that not all implants will have this number of batteries/electronics. In some embodiments, only the electronics and batteries are used to form the thermal channels. However, in other embodiments, control surfaces (not shown) can be utilized to form the channels, wherein the control surfaces only purpose within the implant is to form the channels.

In the embodiment of FIG. 5, to minimize or reduce temperature rise on the surface of the implant due to wireless power transfer, implant 200 can be filled with a thermal medium 214, and the thermal medium can be allowed to flow freely along the thermal channels 216 formed by the spacing of the electronics and batteries or control surfaces. In some embodiments, the thermal medium 214 can be either a fluid or a gas with a significant heat capacity and thermal expansion coefficient that does not change sign in a temperature interval of interest. In some embodiments, the temperature interval of interest ranges from about 37° C. to 50° C. The thermal medium can comprise a low viscosity and a low density for reduced weight. Additionally, a low surface adhesion is desirable so that it does not wick to surfaces, and a high electrical resistivity is desired so as to be electrically inert. One example of a suitable thermal medium would be Fluorinert™ from 3M.

The thermal channels can be oriented to allow the thermal medium to transport heat from the central regions of the implant towards the edges of the housing, due to thermal expansion of the thermal medium and free convection. In some embodiments, the flow paths of the thermal medium are shown by the arrows within the fluid channels of FIG. 5. In the embodiment of FIG. 5, the fluid channels are shown as being arranged horizontally and being substantially parallel, however, when implanted in a patient, the implant would typically be arranged so that the fluid channels are arranged vertically to facilitate convective flow. When arranged vertically, thermal fluid in the central channels would expand and rise up when heated, then cool and flow back down along the side channels. In other embodiments the fluid channels can comprise zigzag, curved, or other unpredictable patterns to extend the length the medium traverses when near the internal walls of the implant. In some embodiments, the fluid flow does not rely on gravity for free convection, but instead can be driven within the implant by a pumping system disposed in the implant.

Figure 6:
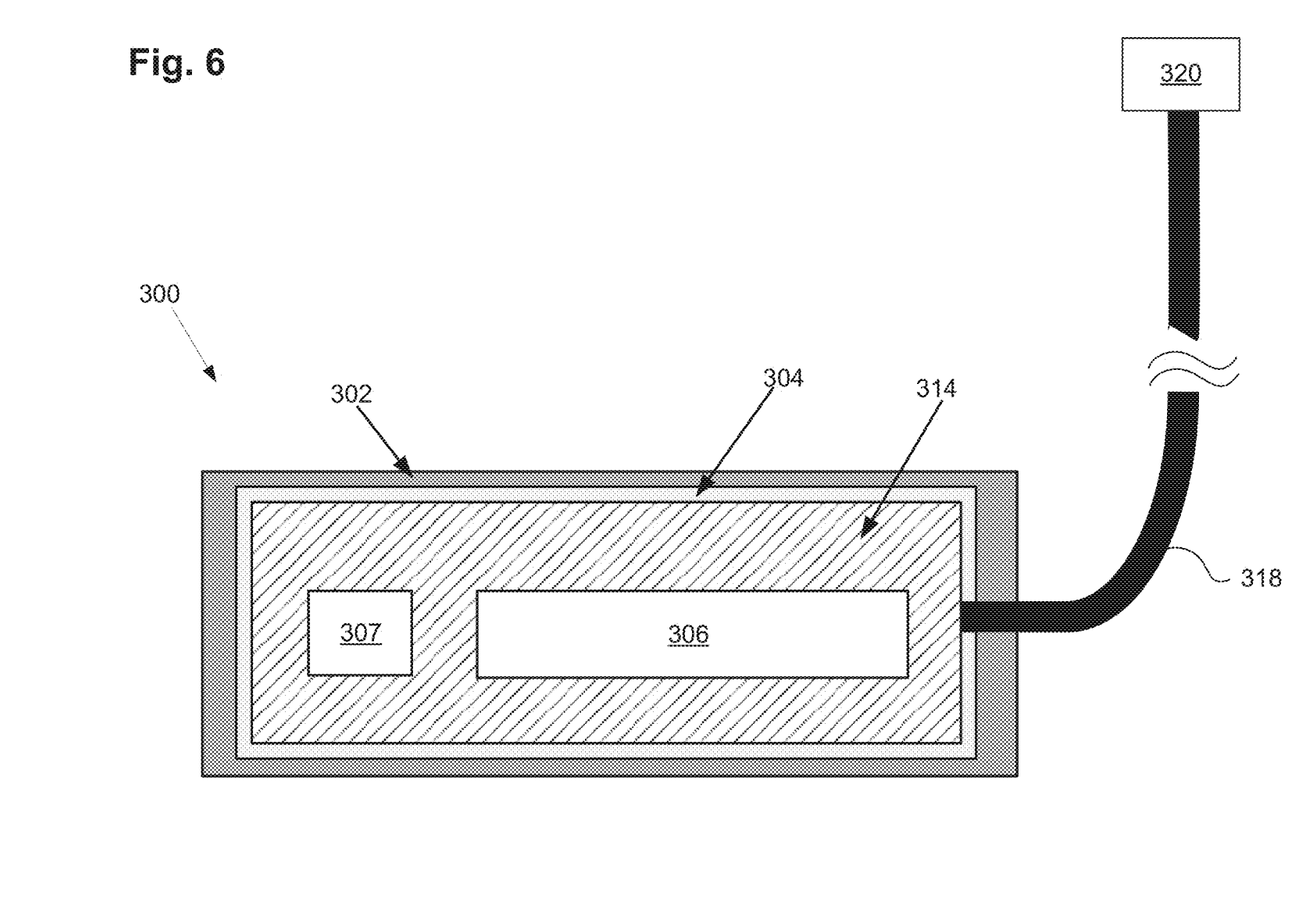
FIG. 6 illustrates yet another embodiment of a TETS implant having a thermal management system.

FIG. 6 illustrates yet another embodiment of a TETS implant 300 having a thermal management system. In FIG. 6, the implant 300 can include housings 302 and 304, electronics 306, and battery 307, similar to housings 102 and 104, electronics 106, and battery 107 described above. The implant can also include a receive coil similar to the coil of FIG. 4A configured for receiving wireless power from an external transmit coil. The interior of implant 300 can be filled with a thermal medium 314. In some embodiments, the thermal medium 314 is chosen to have a boiling point at a temperature greater than 38° C. The thermal medium can comprise a fluid having a low viscosity and a low density for reduced weight. Additionally, a low surface adhesion is desirable so that it does not wick to surfaces, and a high electrical resistivity is desired so as to be electrically inert. Additionally, fluid pipe 318 can be coupled on one end to the interior of the implant and on another end to an implanted medical device 320, such as a blood pump. Fluid pipe 318 can be a flexible tube configured to conform to the body's internal organs during bodily movement. In some embodiments, the fluid pipe can be constructed of an open-cell foam structure.

When the TETS implant 300 generates heat, such as during operation or during wireless power transfer or battery charging, the thermal medium 314 will also rise in temperature. As the thermal medium approaches and surpasses its boiling point, the thermal medium will naturally boil and create vapor. The vapor can be carried vertically by fluid pipe 318 to device 320. When the implant is implanted within a patient, the fluid pipe can be oriented towards the topmost portion of the implant to place it at the furthest point away from gravity. Because of the high energy absorbed during phase change without a rise in temperature, all internal components of the TETS implant and the housings themselves can be kept at or below the boiling temperature of the thermal medium. As the vapor is delivered to the implanted medical device 320, the vapors can condense to form droplets, which can then be pulled by gravity or the fluid pump back towards the TETS implant to absorb more heat.

Instead of dissipating heat to tissue surrounding the TETS implant 300, the heat can be rejected via the fluid pipe towards the other implanted medical device. In the instance where the medical device comprises a blood pump, the heat can be rejected into the blood itself with a known flow rate, set by the pump speed and power, and known thermal properties. This approach allows for higher power electronics enclosed within a smaller volume of TETS implant 300. It also allows the electronics to overcome transient thermal events, such as a momentary high current battery charging operation, without exceeding an enclosure surface temperature specification. Without a thermal medium, either these electronics components would overheat, or the heat generation would cause some portions of the enclosure to rise by more than 2° C., risking damage to local tissue. Additionally, the thermal management system described with respect to FIG. 6 does not require additional thermal management features, such as external fins or internal heat diffusers, allowing the TETS implant to be smaller. This design can result in almost no heat being rejected to the tissue surrounding the TETS implant.

It is important to note that in this embodiment, the implanted medical device 320 must be positioned in the patient's body higher than the implanted position of the TETS implant 300. If the patient orientates himself in a way that puts the implanted medical device 320 below the TETS implant (e.g., the patient lies down with his head below his feet), the system described herein cannot rely on phase change cooling. Instead, the thermal medium must completely fill the fluid pipe between the TETS implant and the implanted medical device. In this embodiment, the TETS implant can be fitted with a pump to actively move the thermal fluid through the fluid pipe.

In yet another embodiment, a thermal sheet could be placed around the box to act as a "heat tube." The lungs of a patient are a large heat conductor, so in some embodiments the thermal sheet could be bent by a surgeon to conform to a lung at the end of an exhale cycle, and the implant could dissipate heat through the sheet into the lungs of the patient.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A power receiver of a wireless power transfer system, comprising:
an implantable housing;
a receiver coil supported by the implantable housing;
electronics disposed within the implantable housing and coupled to the receiver coil, the electronics configured to control wireless power transfer from an external power transmitter to the receiver coil; and
only one insulating layer disposed on an interior surface of the implantable housing and comprising a thermal layer formed of a first material and a central portion formed of a second material, the thermal layer and central portion being positioned in the same plane, the only one insulating layer configured to dissipate heat generated by the electronics and distribute the heat across the only one insulating layer.

2. The power receiver of claim 1, wherein the thermal layer comprises a copper layer.

3. The power receiver of claim 1 wherein the only one insulating layer comprises a thickness of less than 0.5 mm copper.

4. The power receiver of claim 1 wherein the only one insulating layer comprises a thickness of less than 1 mm aluminum.

5. The power receiver of claim 1 wherein the central portion of the only one insulating layer comprises a silicon rubber material.

6. The power receiver of claim 1 wherein the thermal layer comprises a copper layer and the central portion comprises a silicon rubber material.

7. The power receiver of claim 1, wherein the only one insulating layer comprises a ceramic layer embedded in an acrylic polymer matrix.

8. The power receiver of claim 1, wherein the only one insulating layer has a thickness of less than 0.5 mm.

9. The power receiver of claim 1 further comprising an interior layer positioned adjacent to the only one insulating layer.

10. The power receiver of claim 1 further comprising an inner housing disposed within the implantable housing.

11. The power receiver of claim 10 wherein the second material forming the central portion has a higher thermal conductivity along an axis connecting the central portion to the thermal layer than along an axis connecting the central portion to the inner housing, to promote heat spreading toward one or more edges of the implantable housing.

12. The power receiver of claim 1 wherein the second material has a lower thermal conductivity than the first material.

13. The power receiver of claim 1 wherein the first material has a different thermal conductivity than the second material such that the only one insulating layer can direct heat toward one or more edges of the implantable housing.

14. A method of reducing heat transferred to tissue by an implanted wireless power receiver, comprising the steps of:
implanting a wireless power receiver in a patient, the wireless power receiver comprising an implantable housing, a receiver coil supported by the implantable housing, and electronics disposed within the implantable housing and coupled to the receiver coil, the electronics configured to control wireless power transfer from an external power transmitter to the receiver;
receiving wireless power with the wireless power receiver; and
conducting heat generated by the electronics from a central portion of the wireless power receiver towards edges of the wireless power receiver with only one insulating layer disposed on an interior surface of the implantable housing and comprising a thermal layer formed of a first material and a central portion formed of a second material, the thermal layer and central portion being positioned in the same plane.

15. The method of claim 14, wherein the thermal layer comprises at least one copper layer.

16. The method of claim 14, wherein the only one insulating layer comprises a thickness of less than 0.5 mm copper.

17. The method of claim 14, wherein the only one insulating layer comprises a thickness of less than 1 mm aluminum.

18. The method of claim 14, wherein the central portion of the only one insulating layer comprises a silicon rubber material.

19. The method of claim 14, wherein the thermal layer comprises a copper layer and the central portion comprises a silicon rubber material.

20. The method of claim 14 further comprising an interior layer positioned adjacent to the only one insulating layer.

21. The method of claim 14 further comprising an inner housing disposed within the wireless power receiver.

22. The method of claim 21 wherein the second material forming the central portion has a higher thermal conductivity along an axis connecting the central portion to the thermal layer than along an axis connecting the central portion to the inner housing, to promote heat spreading toward one or more edges of the wireless power receiver.

23. The method of claim 14 wherein the second material has a lower thermal conductivity than the first material.

24. The method of claim 14 wherein the first material has a different thermal conductivity than the second material such that the only one insulating layer can direct heat toward one or more edges of the wireless power receiver.

25. A power receiver of a wireless power transfer system, comprising:
an implantable housing;
a receiver coil supported by the implantable housing;
electronics disposed within the implantable housing and couple to the receiver coil, the electronics configured to control wireless power transfer from an external power transmitter to the receiver coil; and
only one insulating layer disposed on an interior surface of the implantable housing and comprising a thermal layer formed of a first material and a central portion formed of a second material, the thermal layer and central portion being positioned in the same plane, the only one insulating layer configured to dissipate heat generated by the electronics to promote heat spreading across the only one insulating layer.

26. The power receiver of claim 25 wherein the central portion of the only one insulating layer comprises a silicon rubber material.

27. The power receiver of claim 25 wherein the thermal layer comprises a copper layer and the central portion comprises a silicon rubber material.

28. The power receiver of claim 25 wherein the only one insulating layer comprises a ceramic layer embedded in an acrylic polymer matrix.

29. The power receiver of claim 25 further comprising an interior layer positioned adjacent to the only one insulating layer.

30. The power receiver of claim 25 further comprising an inner housing disposed within the implantable housing.

31. The power receiver of claim 30 wherein the second material forming the central portion has a higher thermal conductivity along an axis connecting the central portion to the thermal layer than along an axis connecting the central portion to the inner housing, to promote heat spreading toward one or more edges of the implantable housing.

32. The power receiver of claim 25 wherein the second material has a lower thermal conductivity than the first material.

33. The power receiver of claim 25 wherein the first material has a different thermal conductivity than the second material such that the only one insulating layer can direct heat toward one or more edges of the implantable housing.

* * * * *